Dec. 5, 1972 C. G. KLEHM Plant Pat. 3,265
PEONY PLANT
Filed Feb. 1, 1971
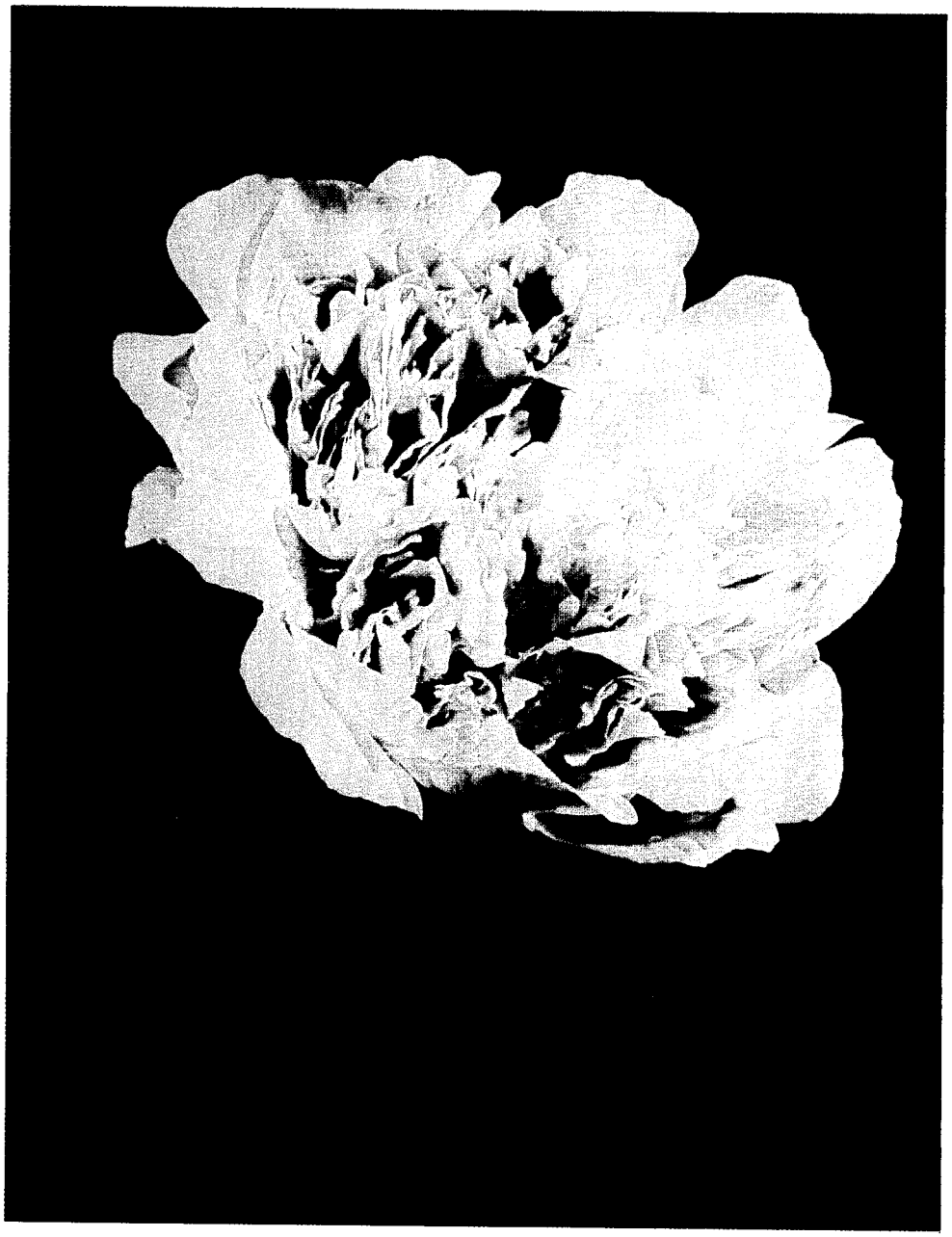
Inventor.
Carl G. Klehm
By: Robb & Robb
Attorneys.

United States Patent Office

Plant Pat. 3,265

Patented Dec. 5, 1972

3,265
PEONY PLANT

Carl G. Klehm, 2 E. Algonquin Road,
Arlington Heights, Ill. 60005

Filed Feb. 1, 1971, Ser. No. 111,772
Int. Cl. A01h 5/00
U.S. Cl. Plt.—68 1 Claim The present invention relates to a new and distinct variety of peony plant of the species botanically known as *Paeonia lactiflora,* which was originated by me by crossing the unpatented peony variety known as "W. L. Gumm" (a large, vigorously double grower bearing flowers having a double-rose type flower form and of white color) with the peony variety known as "Mons. Jules Elie" (unpatented), the former being the male parent and the latter being the female parent.

My new variety resulted from an extensive and prolonged program of breeding and testing conducted by me in an effort to produce new and improved or unique peony varieties, and was selected as one of many outstanding varieties resulting from this breeding program because of its unique combination of the following principal characteristics which distinguish the new variety from its parents, as well as from all other peony varieties of which I am aware:

(1) A healthy, strong and vigorous habit of growth;

(2) Clean, blotch-free and succulent green foliage of attractive appearance;

(3) A ruffled flower form having a shape falling about mid-way between bomb-shaped and double-rose shaped types;

(4) A distinctive and attractive soft and extremely delicate pink flower color; and (5) A suitability for use for garden and landscape plantings, for borders and backgrounds for other plant settings, and for cut-flower uses and exotic arrangements.

Asexual reproduction of my new peony variety by root division, as performed by me in my nursery located at Arlington Heights, Ill., shows that the foregoing characteristics and distinctions come true to form and are established and transmitted through succeeding propagations.

The accompanying drawing shows typical specimens of the vegetative growth and flowers of my new variety, as depicted in color as nearly true as it is reasonably possible to make the same in a color illustration of this character.

The following is a detailed description of the new variety, with color terminology in accordance with the Horticultural Colour Chart (1966 edition), published by The Royal Horticultural Society, of London, England, as based on specimens grown and observed by me at Arlington Heights and Barrington, Ill.:

Breeding: Seedling.
*Seed parent.*—"Mons. Jules Elie."
*Pollen parent.*—"W. L. Gumm."
Propagation: Holds its distinguishing characteristics through succeeding propagations by root division.

FLOWER

Blooming habit: Annual.
Blooming season: Mid-season.
Bud:
*Size.*—Large.
*Form.*—Smooth; round.
*Color.*—Neyron rose, Fan 1, Plate 56C.
*Sepals.*—Even edge. Color: Smooth green.
*Calyx.*—Polysepalous.
*Opening.*—Opens easily and dependably.
Bloom:

*Size.*—Large (averages about 7½ inches when fully expanded).
*Borne.*—Singly; one main bud per stem, with from 1 to 3 auxiliary buds.
*Stems.*—Stout; strong; from 26 inches to 30 inches tall.
*Form.*—Unusual; about mid-way between double-rose type and stereotyped bomb form.
*Petalage.*—Double.
*Color.*—Soft, delicate pink or rose bengal, Fan 1, Plate 56D′.
*Variegations.*—None.
*Discolorations.*—None.
Petals:
*Texture.*—Thick.
*Appearance.*—Exotic.
*Form.*—Ruffled; slightly notched.
*Persistence.*—Above average.
*Fragrance.*—Soft peony.
*Lasting qualities.*—Above average.

REPRODUCTIVE ORGANS

Stamens, anthers: None.
Stamens, filaments: None.
Pollen: None.
Styles: Present in semi-atrophic condition.
Stigmas: Present in semi-atrophic condition.
Ovaries: Present in semi-atrophic condition.
Fruit: None.

PLANT

Form: Bush.
Growth: Helathy; strong; vigorous.
Foliage:
*Leaflets.*—5 or 6 in number.
*Size.*—Medium large.
*Quantity.*—Average.
*Color.*—Clean, blotch-free almond green, Fan 3, Plate 136B′.
*Shape.*—Elliptically acute.
*Texture.*—Dorsal portion is glossy, with pronuonced veins.
*Edge.*—Smooth.
*Serrations.*—None.
*Leaf stem.*—Thick; succulent.
*Stipules.*—None.
*Disease resistance.*—Resistant to leaf blotch and other bacterial peony diseases, as determined by comparison with other varieties for many years as grown at Arlington Heights and Barrington, Ill.

GENERAL OBSERVATIONS

The new peony variety is considered unique primarily because of its unusual flower form and arrangement of the flower petals, and the attractive color of the flowers.

I claim:

1. A new and distinct variety of peony plant of the species botanically known as *Paeonia lactiflora,* substantially as herein shown and described, characterized particularly as to novelty by the unique combination of a healthy, strong and vigorous habit of growth, clean, blotch-free and succulent green foliage of attractive appearance, a ruffled flower form having a shape falling about mid-way between bomb-shaped and double-rose shaped types, a distinctive and attractive soft and extremely delicate pink flower color, and a suitability for use for garden and landscape plantings, for borders and backgrounds for other plant settings, and for cut-flower uses and exotic arrangements.

No references cited.

ROBERT E. BAGWILL, Primary Examiner